(12) United States Patent
Menakuru et al.

(10) Patent No.: US 8,535,947 B2
(45) Date of Patent: Sep. 17, 2013

(54) ON-LINE MONITORING OF DEPROTECTION REACTION IN PEPTIDE AUTOMATED SYNTHESIZER COMPRISING UV DETECTOR

(75) Inventors: Mahendra S. Menakuru, Tucson, AZ (US); Robert William Hensley, Tucson, AZ (US); Joseph B. E. Blais, Tucson, AZ (US)

(73) Assignee: Protein Technologies, Inc., Tucson, AZ (US)

( * ) Notice: Subject to any disclaimer, the term of this patent is extended or adjusted under 35 U.S.C. 154(b) by 430 days.

(21) Appl. No.: 12/895,522

(22) Filed: Sep. 30, 2010

(65) Prior Publication Data

US 2012/0080608 A1   Apr. 5, 2012

(51) Int. Cl.
*G01N 21/00* (2006.01)
(52) U.S. Cl.
USPC .................. 436/164; 436/34; 436/86; 436/89
(58) Field of Classification Search
None
See application file for complete search history.

(56) References Cited

PUBLICATIONS

Fields "Methods for Removing the Fmoc Group" from Methods in Molecular Brology, vol. 35 Peptide Synthesis Protocols Edited by M W Pennington and B. M. Dunn Copyright © 1994 Humana Press Inc, Totowa, NJ, Chapter 2, pp. 17-27.*

Minto et al. "Synthesis and conformational studies of a transmembrane domain from a diverged microsomal Δ12-desaturase", Analytical Biochemisrty, 2002, v. 308, pp. 134-140.*

Nagarkar and Schneider "Synthesis and Primary Characterization of Self-Assembled Peptide-Based Hydrogels", Methods Mol Biol. 2008, v. 474, pp. 61-77.*

Glaser "Competition Mounting in Peptide Market", GEN: Genetic Engeneering & Biotechnology News, Jul. 2009, v. 29. No. 3, Feature Articles, no page numbers.*

"Improved Technologies for Peptide Synthesis: New Methods for UV-Monitoring and Robotic Peptide Library Synthesis" (Protein Technology Incorp., no date), PharManufacturing: The International Peptide Review, 2010, pp. 22-24; http://peptidereview.com/PDF/PTI%20UV%20and%20Robotic_IPR.pdf.*

* cited by examiner

*Primary Examiner* — Yelena G Gakh
(74) *Attorney, Agent, or Firm* — Quarles & Brady LLP; Gavin J. Milczarek-Desai

(57) ABSTRACT

A method for on-line monitoring of deprotection reaction in a peptide automated synthesizer comprising UV detector is disclosed. A UV source, detector, electronics, and housing are integrated with a line or tube through which liquid reactants flow for periodic measurements in the peptide synthesizer. The method includes determining the progression of the reaction, completion point of the reaction, and the modification of the reaction times and repetitions in real time.

16 Claims, 9 Drawing Sheets

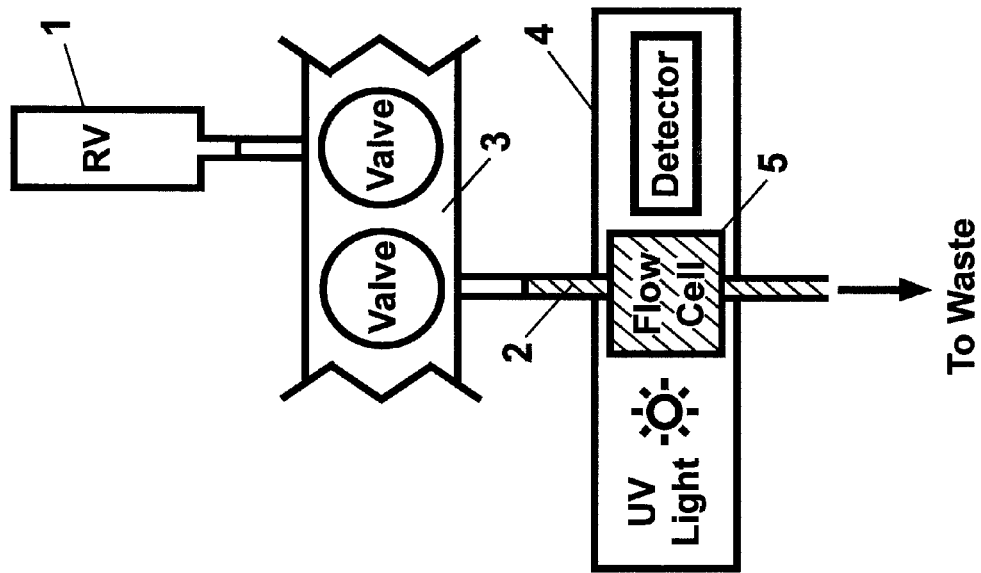
Figure 1A: Prior Art
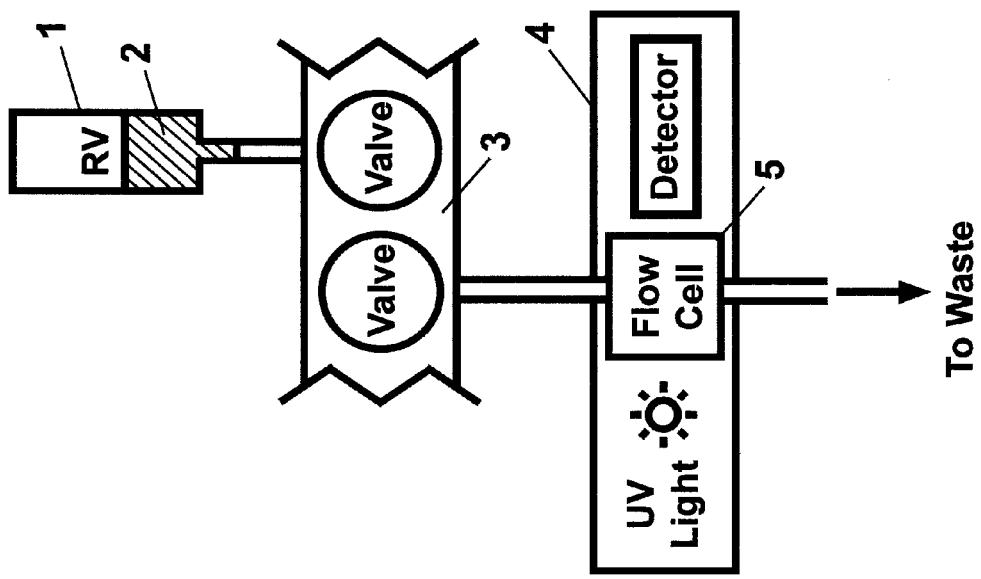
Figure 1B: Prior Art

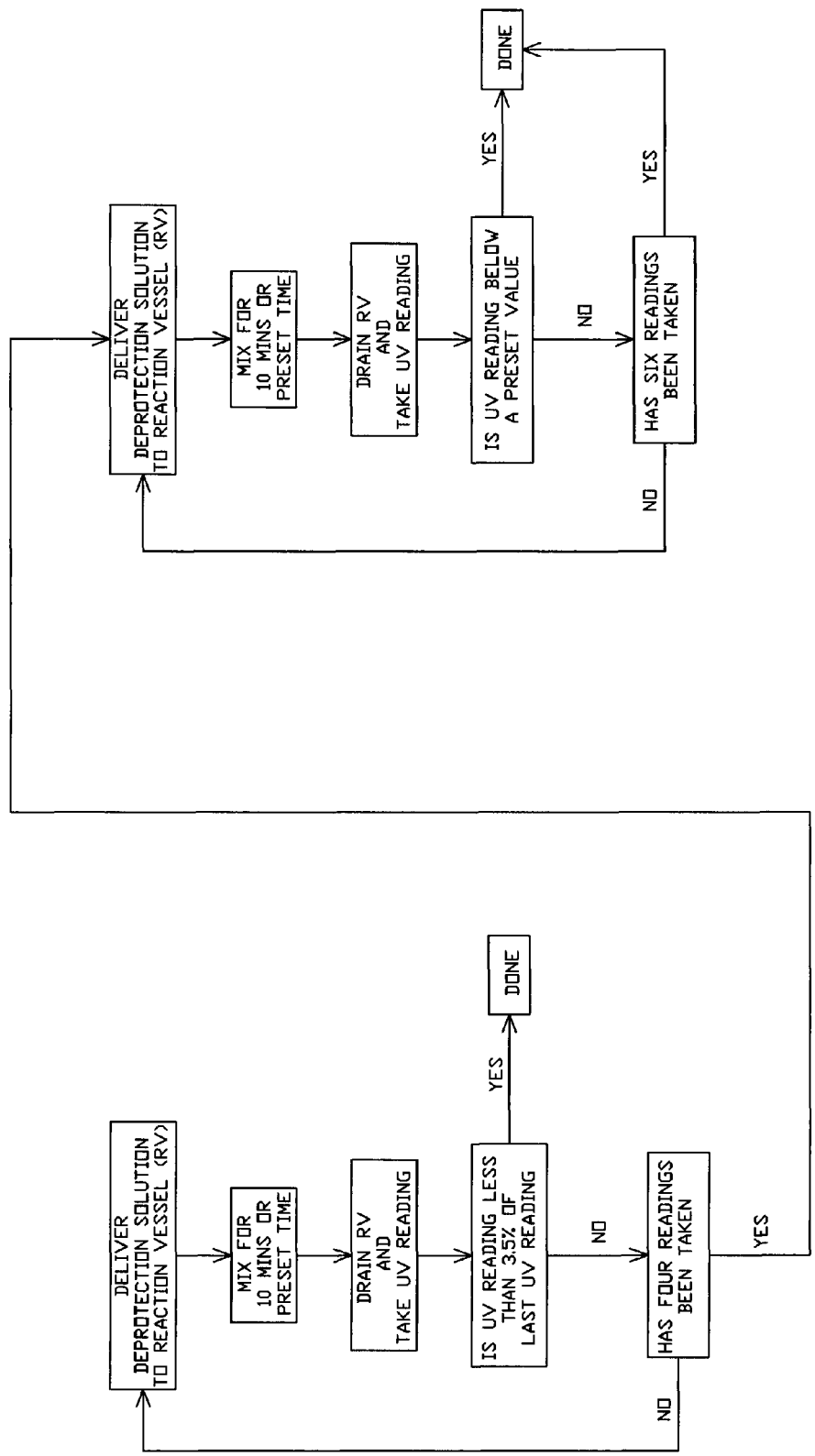
FIG 2, PRIOR ART

ON-LINE MONITORING OF DEPROTECTION REACTION IN PEPTIDE AUTOMATED SYNTHESIZER COMPRISING UV DETECTOR

BACKGROUND OF THE INVENTION

1. Field of the Invention

The invention relates in general to the monitoring of chemical reactions during automated synthesis and more specifically in a preferred embodiment to an online system and method for monitoring, for example, fluorenylmethyloxycarbonyl (Fmoc) deprotections during peptide synthesis.

2. Description of the Related Art

It is known in the art to synthesize biological products through automated synthesis. For example, automatic apparatus for solid phase peptide synthesis (SPPS) have become very popular for the production of naturally occurring and artificial peptides and proteins. The general principle of SPPS is one of repeated cycles of coupling and deprotection. In essence, the free N-terminal amine of a peptide attached to a solid-phase support is coupled to the carboxyl end of a single N-terminal protected amino acid. This newly coupled amino acid is then deprotected, revealing a new N-terminal amine to which a further protected amino acid may be attached.

The 9-fluorenylmethyloxycarbonyl (Fmoc) group is commonly used as a protecting group for primary and secondary amines. The Fmoc group can be incorporated by reacting the amine with reagents of the general structure Fmoc-X, such as 9-fluorenylmethyl chloroformate (Fmoc-Cl) and 9-fluorenylmethyl succinimidyl carbonate (Fmoc-OSu). Once attached, the Fmoc protecting group is stable to acid, but labile to bases such as piperidine (see below).

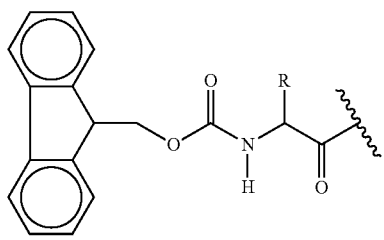

Fmoc-Amino Acid-Resin

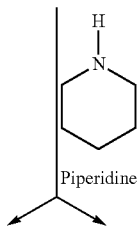

Piperidine

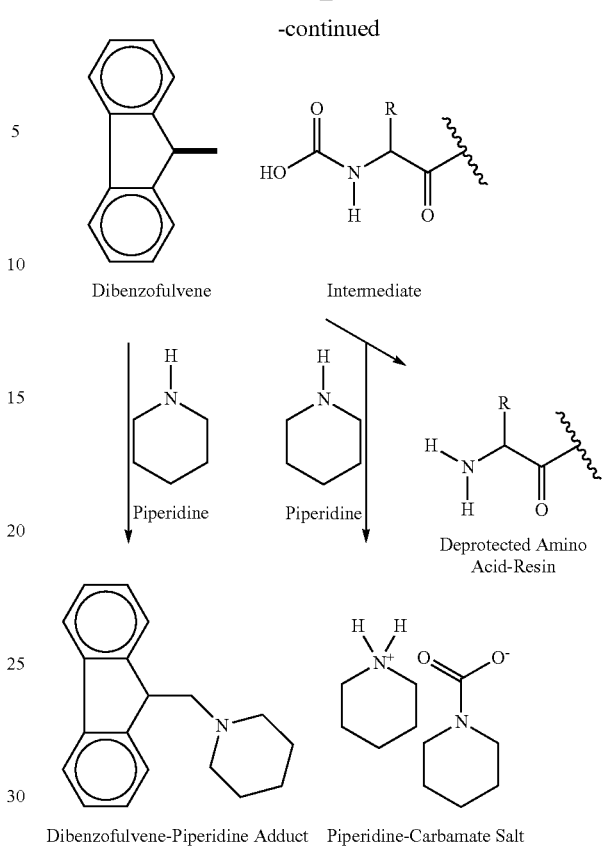

These characteristics are particularly useful in solid phase peptide synthesis because the removal of the Fmoc group with piperidine does not interfere with the acid labile linker attaching the peptide to the solid phase.

References:
1) Chinchilla R, Dodsworth D J, Najera C, Soriano J M. A new polymer supported reagent for the Fmoc-protection of amino acids. *Tet. Lett.* 2001; 42: 7579-7581.
2) Paquet A. Introduction of 9-fluorenylmethyloxycarbonyl, trichloroethoxycarbonyl, and benzyloxycarbonyl amine protecting groups into O-unprotected hydroxyamino acids using succinimidyl carbonates. *Can. J. Chem.* 1982; 60: 976-980.

Given that the ultimate yield of a synthesized product depends on the yield of each step of the synthesis process, the coupling of amino acids during SPPS must be highly optimized. Because the extent of deprotection is a crucial parameter in SPPS, it often must be repeated until "complete," i.e., as much deprotection has occurred as is likely to such that further repetition is considered wasteful. Thus, various ways of monitoring the extent of the completion of the deprotection reaction have been developed.

For example, Fmoc deprotection has been monitored via conductivity assays. However, it has been found that sensitivity to conductive impurities, among other reasons, can lead to unnecessary repetition of the deprotection reaction and the resulting excess of time, reagent consumption, and lower yield.

A more sensitive approach to monitoring deprotection involves the use of ultraviolet (UV) light at 365 nm to measure the adsorption of the dibenzofulvene-piperidine adduct formed during the deprotection reaction. Unfortunately, this method also has significant drawbacks relating to artificial readings caused by undesired adsorption by other reagents such as triazole-based coupling reagents. Subsequently, the use of UV light at 301 nm to measure the adsorption of deprotection reagents and/or adducts has been found to be more advantageous.

Known apparatus and methods of UV monitoring at 301 nm involve the use of a flow cell, UV source and detector that is external to the synthesizer, and, thus, rely on moving liquid reagents from the reactor to the detector's flow cell at the conclusion of a deprotection reaction. This requires extra chemical rinsing between UV measurements to clear lines and remove bubbles. In addition, flow rates through the cell can affect the measurement accuracy and wait periods must be inserted prior to and after a reading for the values to stabilize. The extra use of reagents and extra time required make the method uneconomical at a scale greater than 1.0 mmol. Moreover, because the UV measurements are performed offline (upon conclusion of the deprotection reaction cycle), adjustments cannot be made in real time to the length of deprotection reactions, resulting in longer than necessary reaction times.

Thus, there is a need for on-line monitoring systems and methods to more efficiently produce synthesized products of high quality and yield.

SUMMARY OF THE INVENTION

The deprotection monitoring systems, devices and methods of the invention involve an on-line UV source and detector apparatus that makes UV measurements possible during the deprotection reaction step such that modification of deprotection times and repetitions can be made in real time. This has been achieved through the integration of a UV monitoring system within the automated synthesizer itself.

Preferably, embodiments of UV monitoring devices are integrated proximally to the reaction vessel in which the deprotection reaction takes place, for example, in the line just below the reaction vessel. Thus, the reaction fluid is moved a short distance from the reaction vessel to the UV monitoring system at specified time intervals (e.g., every 10 seconds), measured for deprotection progression and completion, and replaced in the reaction vessel. Also, no special rinsing is required due to the UV measurement flow cell being the line through which rinsing reagents for the reactor would normally flow.

Additional features and advantages of the invention will be forthcoming from the following detailed description of certain preferred embodiments when read in conjunction with the accompanying drawings.

BRIEF DESCRIPTION OF THE DRAWINGS

FIGS. 1A and 1B illustrate a prior art device for UV deprotection monitoring.

FIG. 2 is a flow diagram for a prior art method for the UV monitoring of deprotection reactions.

DETAILED DESCRIPTION OF THE PREFERRED EMBODIMENT

Figure 3B:
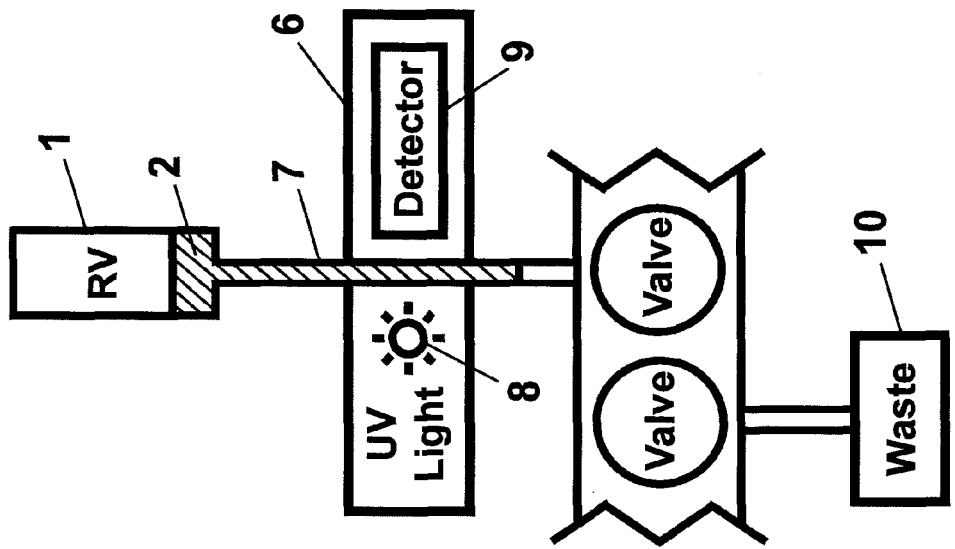
FIGS. 3A and 3B illustrate a device of deprotection monitoring using UV light in accordance with an embodiment of the invention.

What has been the state-of-the-art in monitoring deprotection reactions is shown in FIGS. 1A and 1B. This method of monitoring involves the use of ultraviolet (UV) light at 301 nm to measure the adsorption of deprotection reagents and/or adducts. Known apparatus and methods of UV monitoring at 301 nm involve the use of an UV monitoring instrument that is external to the synthesizer, and, thus, rely on moving liquid reagents from the reaction vessel 1 to an external monitor 4 at the conclusion of a deprotection reaction. Accordingly, the deprotection reagents 2 typically pass through valves 3 and flow cell 5, which means extra rinses of the lines are needed between UV measurements to clear material and bubbles therefrom, and do not return to the reaction vessel 1.

Measuring the extent of deprotection at an external UV monitor 4 is not a trivial undertaking, requiring constant nitrogen and N-methylpyrrolidinone (NMP) flow-rates, which must be calibrated before a synthesis occurs. Moreover, taking only one measurement at the end of the deprotection reaction means that the length and timing of the deprotection reaction cannot be controlled (only measured as to extent of completion).

FIG. 2 shows in flow diagram the current state of the art method for determining the completion of the deprotection reaction. As depicted in FIGS. 1A and 1B, a quantity of deprotection solution 2 is delivered to the reaction vessel 1 and mixed for a preset time. The fluid is then transferred to an external UV measurement device 4. After the measurement the fluid is transferred to waste. As shown in FIG. 2, if the UV measurement is less than 3.5% of the previous UV reading the deprotection reaction is considered complete. If the UV measurement is greater than 3.5% of the previous UV measurement, another quantity of deprotection solution is delivered to the reaction vessel. This cycle continues until the current UV measurement is less than 3.5% of the previous UV measurement or four deprotection solution deliveries/UV measurements have been taken. If these conditions are never reached, a second loop of deprotect deliveries/UV measurements is started. This loop continues until the UV reading is less than a preset value or six additional deliveries have been made.

Figure 3A:
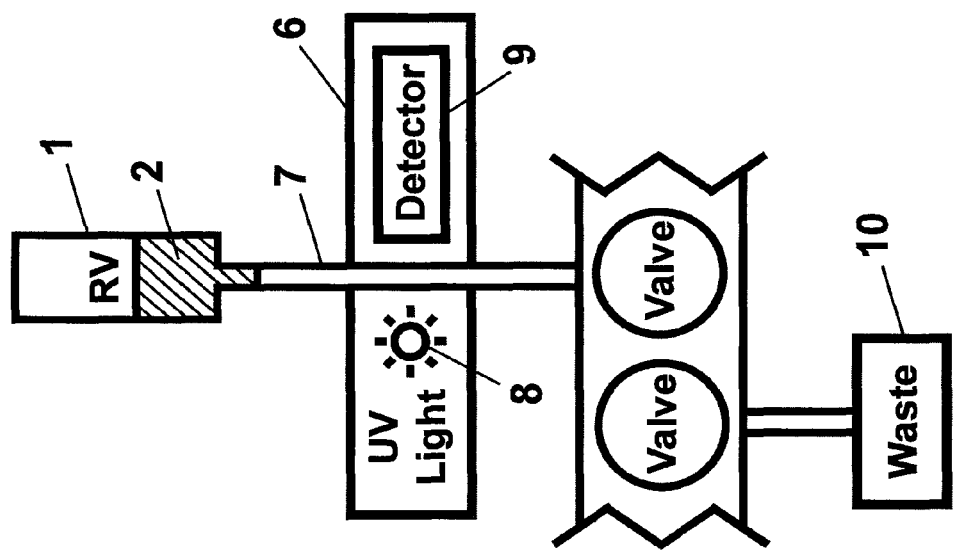

FIGS. 3A and 3B, in contrast, schematically illustrate in simplified form an embodiment of the invention that provides real-time UV monitoring and control of the deprotection reaction via an integrated monitoring system. Reaction vessel 1 contains deprotection reagents 2. At specified time intervals, the deprotection reagents 2 are pushed by nitrogen to the UV measurement device 6 and tube 7 located proximally to the reaction vessel 1. Preferably, the UV measurement tube 7 is disposed directly below the reaction vessel 1 inside the synthesizer such that deprotection reagents 2 are partially maintained within the reaction vessel during a measurement (FIG. 3B). Upon conclusion of a measurement, the deprotection reagents are either returned to the reaction vessel 1 for further reaction with the solid-phase reactants (FIG. 3A) or are sent to waste 10 if the reaction reaches completion or another stopping point as illustrated by the flow diagram FIG. 4.

While other arrangements are possible, preferably a UV measurement apparatus 6 is disposed about the UV measurement tube 7 such that a UV source 8 (e.g., an LED UV source) and UV detector 9 are configured to measure UV adsorption at 301 nm of deprotection reagents 2 or adducts of the same. Thus, an on-line UV source and detector are provided that record data at specified time intervals during the deprotection reaction and not just at the end, which provides an automatic means for modifying deprotection times and repetitions based on the methods shown in the flow diagram in FIG. 4.

In addition, the apparatus of the invention requires no extra or special rinsing routines because the UV measurement tube 7 is itself the UV measurement cell, meaning that it gets rinsed when the solid phase support in the reaction vessel gets rinsed. Furthermore, periodic UV measurement taking does not interfere with the reaction in the reaction vessel or require special flow calibrations or pressure adjustments.

Figure 5:
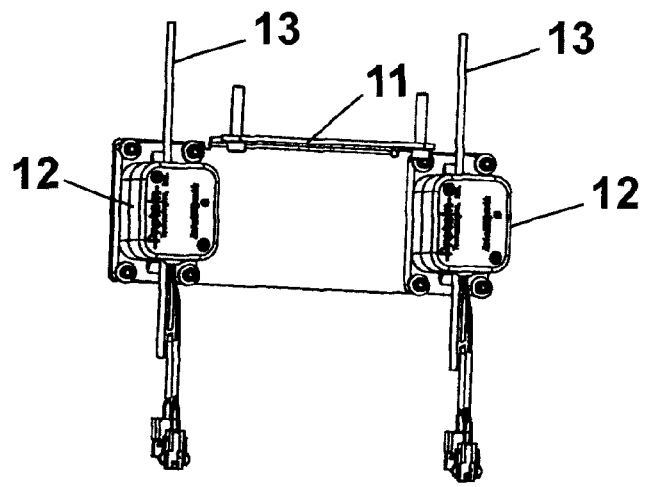
FIG. 5 shows an assembled module embodiment of the invention in elevational view.

Turning to FIG. 5, an assembled module 11 is shown that has two UV measurement apparatus 12 suitable for installation below reaction vessel area 1 shown in FIG. 3 and around UV measurement tubes 13.

Figure 6:
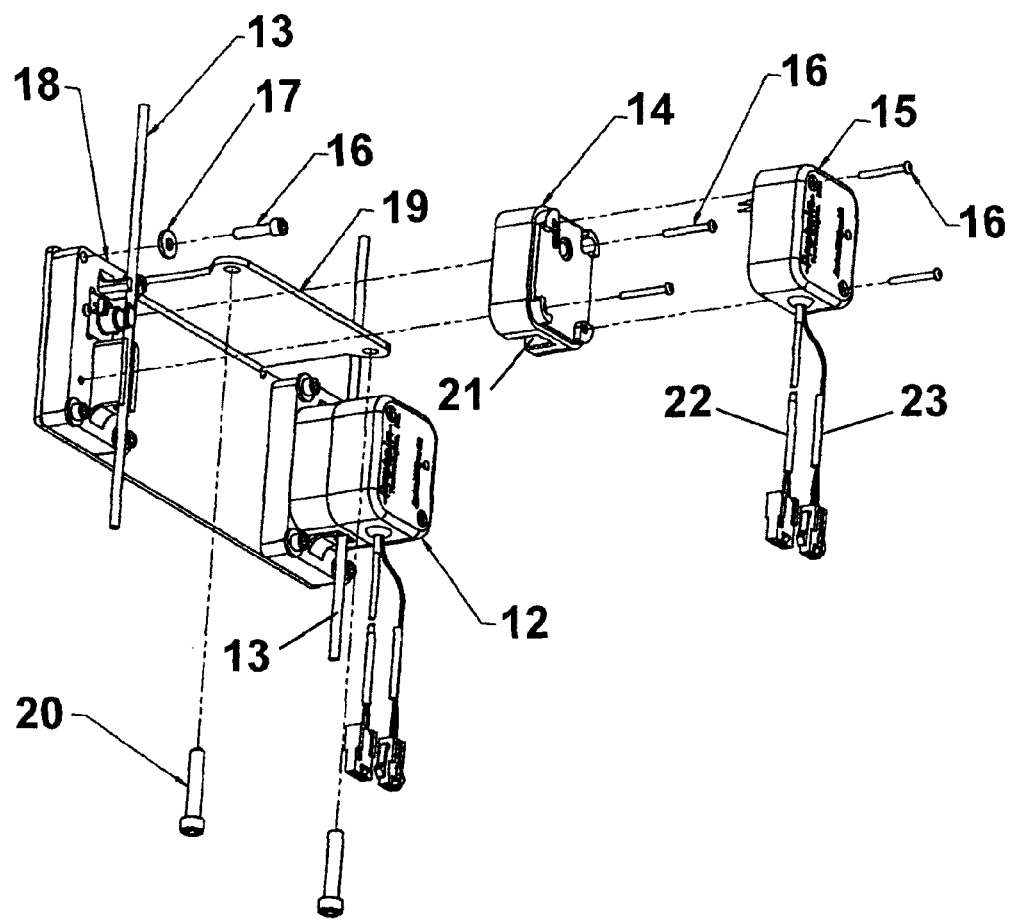
FIG. 6 is an enlarged, partly assembled, perspective view of the FIG. 5 embodiment.
Figure 7:
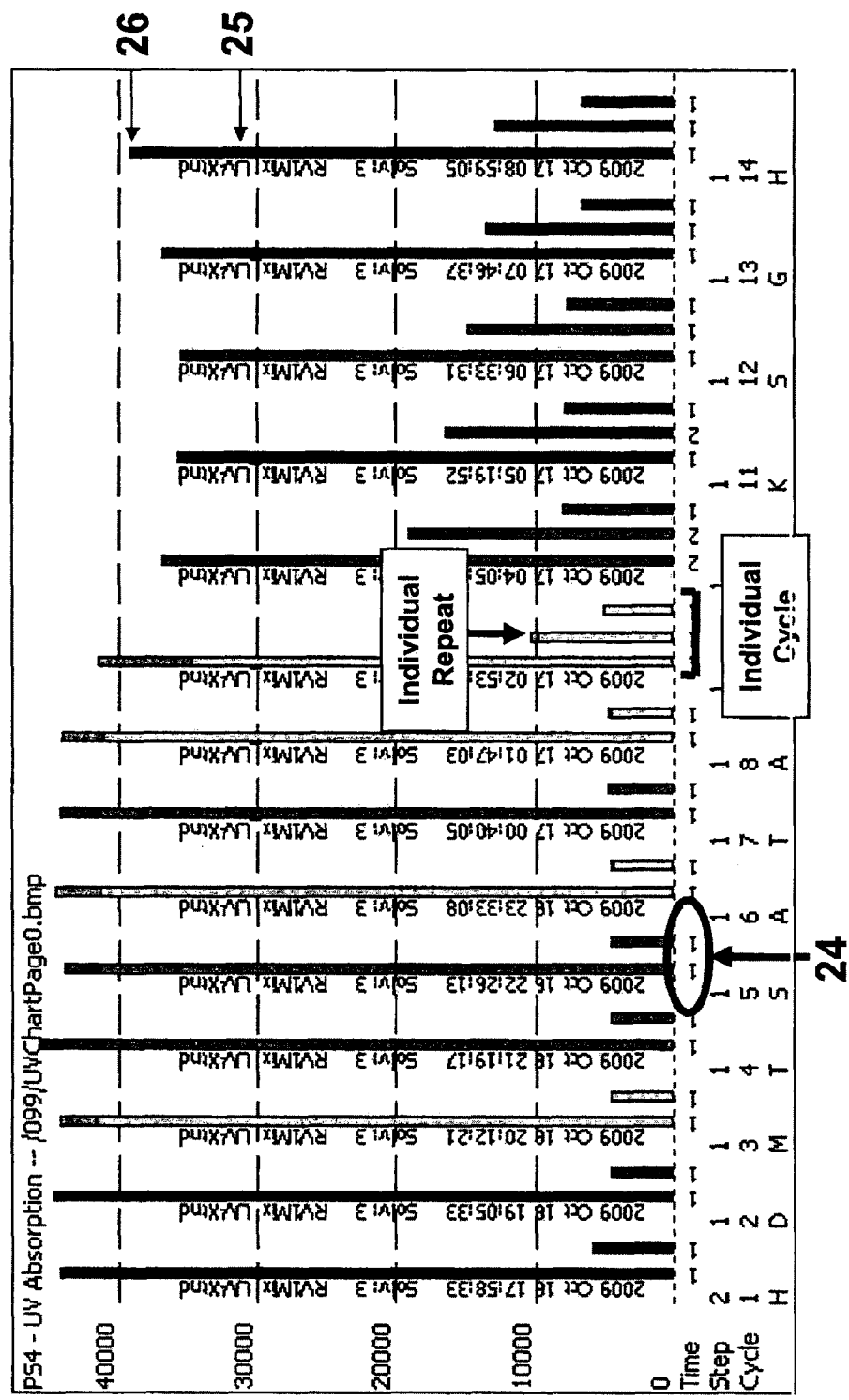
FIGS. 7-10 are examples of information and data that may be generated according to the apparatus and methods of the invention.
Figure 8:
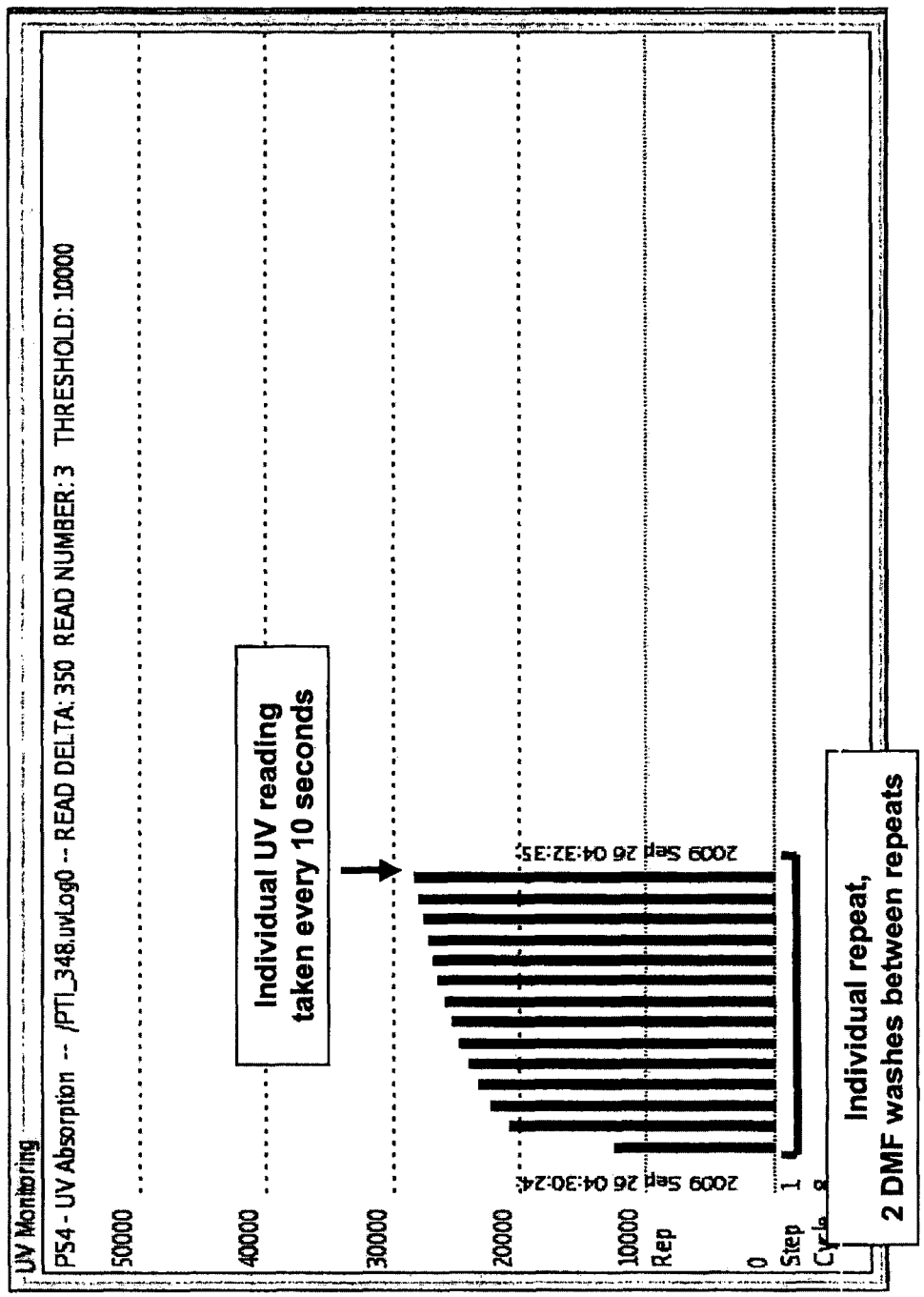

As seen in greater detail in the enlarged, partly assembled, perspective view of FIG. 6, UV measurement apparatus 12 is preferably disposed around UV measurement tube 13 by securing half 14 of the apparatus 12 with half 15 via fastener 16 and washer 17 to mounting bracket 18. Top 19 of mounting bracket 18 may then be attached to reaction vessel mount via fasteners 20 as shown in FIG. 6.

Measuring apparatus half 14 contains a groove 21 on its front side that provides a void into which UV measuring tube 13 is located. While other configurations are possible, half 14 has a UV source on one side of groove 21 and a UV detector on the other side, while half 15 contains wiring and interface cables 22 and 23 for connecting the apparatus 12 to the power supply and computer processor of the synthesizer (not shown).

Figure 4:
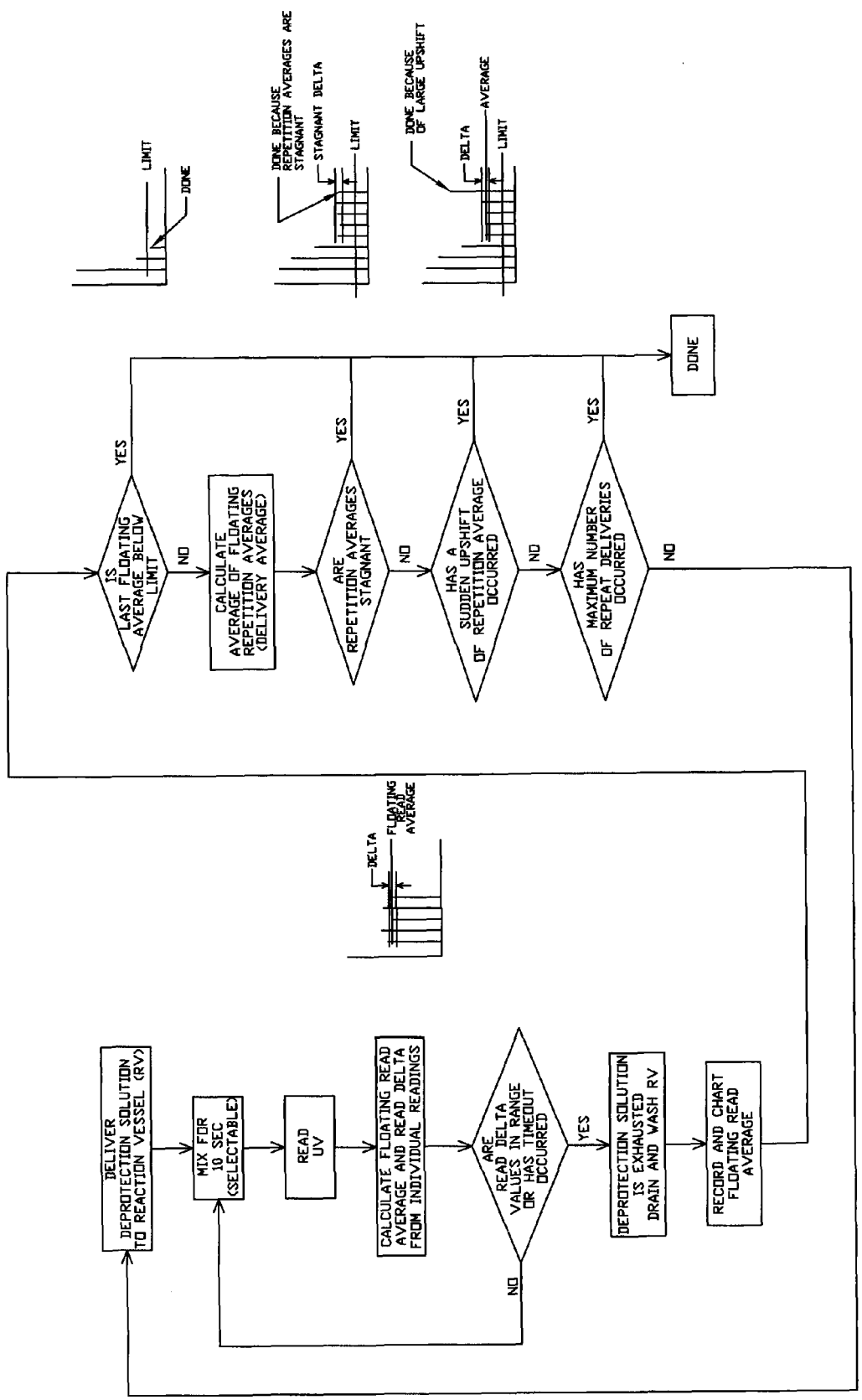
FIG. 4 is a flow diagram for a method for the UV monitoring of deprotection reactions in accordance with the present invention.

Turning to applications of and methods involving the invention, FIG. 4 shows a logic flow diagram of the methods. During each deprotection solution delivery, the deprotection solution is pushed down to the UV sensor every 10 seconds or an alternative time as selected by the user. The rate at which the reaction is progressing is determined by calculating a floating average of a specified number of previous readings. When the floating average does not change more than a preselected delta, the deprotection chemical is exhausted, no longer effective for the process, and the fluid is sent to waste and fresh deprotection solution is delivered.

Prior art methods have no means to determine when the deprotection solution is exhausted and use a fixed mixing time. Since the deprotection step requires multiple deliveries of deprotection solution, a method is required to determine when the deprotection step is complete. As shown in FIG. 4, the completion criteria are (1) is the floating average of UV adsorption readings below a set limit, (2) has the process reached a stagnant state where further deliveries will not be effective, (3) has a high UV reading occurred, and (4) has a user-set limit on the number of deprotection deliveries been reached. Prior art methods only checked for criteria (1) and (4). Criteria (2) and (3) are new and useful in accordance with the methods of this invention. The addition of these criteria can greatly reduce the amount of deprotection solution usage and reaction times.

FIGS. 7-10 depict examples of information and data that may be generated in conjunction with an automated, programmable synthesizer, such as those available from Protein Technologies, Inc., Tucson, Ariz., USA.

In an exemplary use of the apparatus of the invention with a synthesizer, one of three UV-monitoring modes may be selected: (1) basic monitoring mode, which measures the extent of the deprotection reaction but does not adjust or otherwise change the synthesis reaction, (2) deprotection monitoring with feedback mode, which measures the extent of the deprotection reaction and uses that data to control the deprotection reaction times and repetitions, and (3) deprotection and coupling monitoring with feedback mode, which measures the extent of the deprotection reaction and uses that data to control the deprotection reaction times and repetitions, as well as to extend the coupling times, accordingly.

In all modes, an adsorption reading is taken every 10 seconds or an alternative time as selected by the user during the deprotection reaction. Two types of graphical data representations can be generated: A synthesis summary of FIG. 7 or an individual deprotection reaction of FIG. 8. The synthesis summary displays the reaction time 24 below each peak, and indicates the minimum 25 and maximum 26 adsorption readings within each peak.

Figure 9:
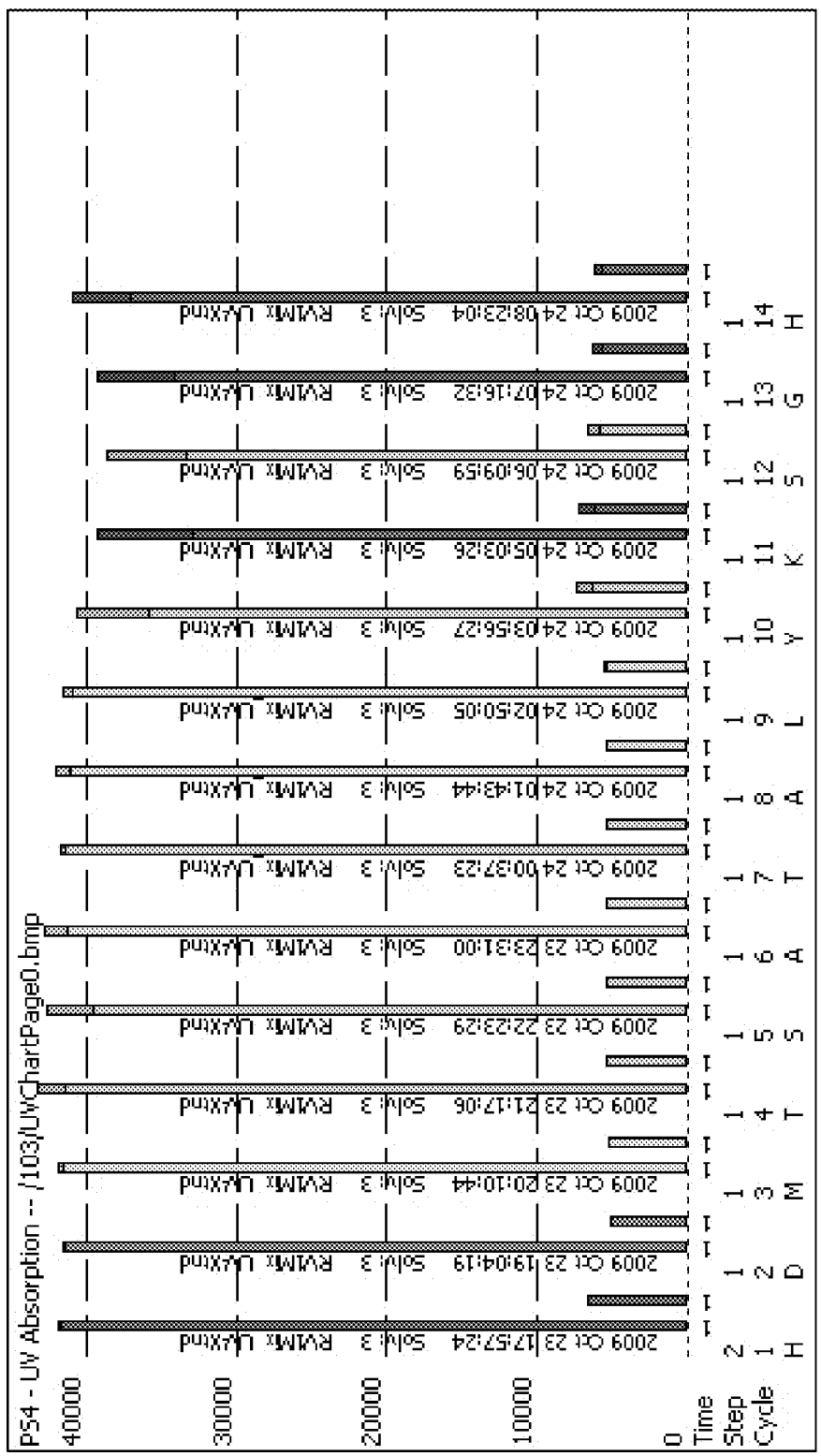

In the basic monitoring mode, UV measurement data is taken during the deprotection reaction without altering or adjusting the synthesis (FIG. 9).

Figure 10:
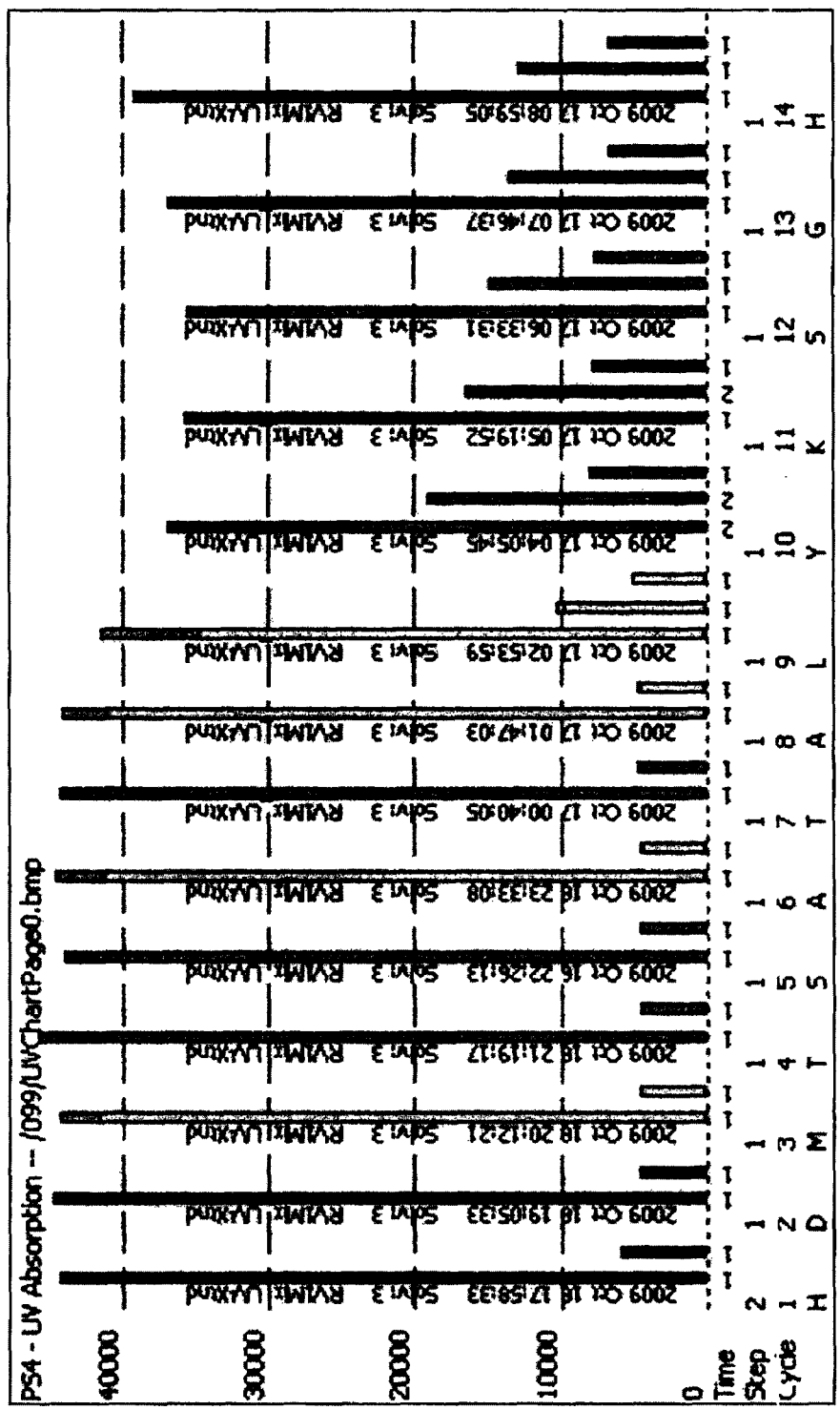

In deprotection with feedback mode, UV measurement data is used to extend or reduce the deprotection time and number of repetitions without affecting any other steps in the cycle (FIG. 10).

Thus, the new and inventive aspects of the apparatus and methods of the invention are readily apparent. In addition to the advantages described above, real-time data during a synthesis can be used to contemporaneously generate graphs of individual deprotection reactions or overall summaries for a synthesis. Moreover, difficult reaction steps can be identified during as well as after a synthesis.

Various modifications are possible within the meaning and range of equivalence of the appended claims.

What is claimed is:

1. A method for real-time monitoring the deprotection reaction of a Fmoc protecting group in a peptide automated synthesizer to obtain feedback on reaction completion during said deprotection reaction, comprising the steps of:
    (a) within said automated synthesizer, which includes an ultraviolet (UV) source and UV sensor, periodically pushing a deprotection solution comprising dibenzofulvene and related adducts and byproducts from said reaction to the UV sensor in an area that is adapted to transmit UV light and irradiating it with UV light at a wavelength of about 301 nm;
    (b) detecting the absorption of said UV light and determining the rate at which the reaction is progressing by calculating a floating average of a specified number of previous readings; and
    (c) determining the reaction completion when the floating average does not change more than a preselected delta.

2. The method of claim 1, wherein said deprotection reaction time is extended based on absorption data recorded during said detecting in step (b), with said data used to determine the extent of completion of the deprotection reaction.

3. The method of claim 1, wherein said deprotection reaction is repeated based on absorption data recorded during said detecting in step (b), with said data used to determine the extent of completion of the deprotection reaction.

4. The method of claim 1, wherein the time of a subsequent amino acid or monomer coupling reaction is extended based on the time of said deprotection reaction, itself dependent on the absorption data recorded during said detecting in step (b).

5. The method of claim 1, wherein said area is a UV transmissive tube.

6. The method of claim 1, wherein steps (a) and (b) are performed at specified time intervals during said reaction.

7. The method of claim 1, further comprising the step of providing a visual output of absorption data acquired during the Fmoc deprotection steps of the synthesis.

8. The method of claim 7, wherein said visual output of absorption data comprises a graphical synthesis summary or a graphical representation of an individual deprotection reaction.

9. A method for real time monitoring the deprotection reaction of a Fmoc protecting group in a peptide automated synthesizer to obtain feedback on reaction completion during said deprotection reaction, the synthesizer having a reaction vessel, an ultraviolet (UV) source and UV sensor within said synthesizer, and a UV-transmissive tube disposed in fluid connection with and proximally to said reaction vessel, comprising the steps of:
   (a) periodically drawing a liquid containing dibenzofulvene and realated adducts and byproducts from said reaction vessel into said UV-transmissive tube,
   (b) irradiating said liquid with UV light at a wavelength of about 301 nm,
   (c) detecting through said UV sensor the absorption of said UV light and determining the rate at which the reaction is progressing by calculating a floating average of a specified number of previous readings; and
   (d) returning said liquid to the reaction vessel unless reaction completion is indicated when the floating average does not change more than a preselected delta.

10. The method of claim 9, wherein the step of drawing a liquid from the reaction vessel occurs during said reaction.

11. The method of claim 9, wherein steps (a) thru (d) are performed at specified time intervals during said reaction.

12. The method of claim 9, wherein the time of the deprotection reaction is extended based on the absorption data recorded during said detecting in step (c), with said data used to determine the extent of completion of the deprotection reaction.

13. The method of claim 9, wherein the deprotection reaction is repeated based on the absorption data recorded during said detecting in step (c), with said data used to determine the extent of completion of the deprotection reaction.

14. The method of claim 9, wherein the time of a subsequent amino acid or monomer coupling reaction is extended based on the time of said deprotection reaction, itself dependent on the absorption data recorded during said detecting in step (c).

15. The method of claim 9, further comprising the step of providing a visual output of the absorption data during the synthesis.

16. The method of claim 15, wherein said visual output of absorption data comprises a graphical synthesis summary or a graphical representation of an individual deprotection reaction.

* * * * *